United States Patent [19]

Clipper et al.

[11] 4,431,631

[45] Feb. 14, 1984

[54] AQUEOUS ORAL SOLUTION

[75] Inventors: Donald Clipper, Belle Mead; James Norfleet, Plainfield, both of N.J.

[73] Assignee: Colgate-Palmolive Company, New York, N.Y.

[21] Appl. No.: 455,388

[22] Filed: Jan. 3, 1983

[51] Int. Cl.$^3$ .................. A61K 7/20; A61K 33/40
[52] U.S. Cl. ..................... 424/53; 424/130; 426/651
[58] Field of Search .............. 424/53, 130; 426/651

[56] References Cited

U.S. PATENT DOCUMENTS

| | | | |
|---|---|---|---|
| 959,605 | 5/1910 | Queisser | 424/130 |
| 2,035,267 | 3/1936 | Fleischman | 424/53 |
| 2,054,742 | 9/1936 | Elbel | 424/53 |
| 2,422,145 | 6/1947 | Taylor | 426/651 |
| 2,435,744 | 2/1948 | Hartman | 426/651 |
| 2,501,145 | 3/1950 | Smith | 424/53 |
| 2,508,978 | 5/1950 | Tribble | 426/651 |
| 2,677,700 | 5/1954 | Jackson | 424/49 |
| 2,773,801 | 12/1956 | Fox | 424/49 |
| 3,639,563 | 2/1972 | Janvszewsky | 424/49 |
| 3,639,574 | 2/1972 | Schmolka | 424/130 |
| 3,666,496 | 5/1972 | Honey et al. | 426/651 |
| 3,674,502 | 7/1972 | Honey et al. | 426/651 |
| 3,907,991 | 9/1975 | Accetta | 424/130 |
| 3,947,570 | 3/1976 | Pensak et al. | 424/49 |
| 3,954,974 | 5/1976 | Herzog et al. | 424/130 |
| 4,130,638 | 12/1978 | Dhabhar et al. | 424/49 |
| 4,150,151 | 4/1979 | Paper et al. | 424/49 |
| 4,216,200 | 8/1980 | Horn | 424/52 |
| 4,226,851 | 10/1980 | Sompayrac | 424/53 |
| 4,272,513 | 6/1981 | Gaffar | 424/52 |
| 4,278,664 | 7/1981 | Van Cleave | 424/130 |

FOREIGN PATENT DOCUMENTS 2944021 5/1980 Fed. Rep. of Germany .

OTHER PUBLICATIONS

Kaizu et al. Bull. Tokyo Dent. Coll. (1978) 19(4):209–216 (Eng.) Reduction of Bad Breath from Periodontal Patients by Dilute Hydrogen Peroxide Solution.

Schmolka American Perfurmer & Cosmetics 82: 25–30, Jul. 1967, "Applications of Pluronic Polyols in the Cosmetic Industry".

*Primary Examiner*—Shep K. Rose
*Attorney, Agent, or Firm*—Norman Blumenkopf; Herbert S. Sylvester; Murray M. Grill

[57] ABSTRACT

An aqueous oral solution containing hydrogen peroxide, glycerin and/or sorbitol, Pluronic-type surfactant, polyoxyethylenated sorbitol monofatty acid ester surfactant, sweetener and selected flavor.

17 Claims, No Drawings

AQUEOUS ORAL SOLUTION

This invention relates to an aqueous oral solution and especially to a peroxide-containing aqueous mouthwash or mouthrinse solution.

It has long been recognized in the art that hydrogen peroxide and other peroxygen-containing agents are effective in curative and/or prophylactic treatments with respect to caries, dental plaque, gingivitis, periodontitis, mouth odor, tooth stains, recurrent aphthous ulcers, denture irritations, orthodontic appliance lesions, postextraction and postperiodontal surgery, traumatic oral lesions and mucosal infections, herpetic stomatitis and the like. Peroxide-containing agents in the oral cavity exert a chemomechanical action generating thousands of tiny oxygen bubbles produced by interaction with tissue and salivary enzymes. The swishing action of a mouthrinse enhances this inherent chemomechanical action. Such action has been recommended for delivery of other agents into infected gingival crevices. Peroxide mouthrinses prevent colonization and multiplication of anaerobic bacteria known to be associated with periodontal disease.

It is however also known that most peroxy compounds such as hydrogen peroxide and metal peroxides such as magnesium peroxide in such oral compositions, by interaction with other common excipients therein, tend to be unstable in storage, continuously losing the capacity to release active or nascent oxygen over relatively short periods of time, and tend to diminish or destroy the desired function of such excipients. Among such excipients are flavors and coloring agents added to enhance the acceptability of the mouthrinse to those in need of an oral peroxidizing treatment. Numerous proposals have been made for solving the aforementioned problems, including encapsulating the peroxide compound and/or the peroxide-sensitive excipient, using more stable but more expensive peroxy compounds such as organic peroxides and peroxydiphosphate salts (e.g. the tetrapotassium salt), etc.

It is an object of this invention to provide an oral solution which will not be subject to one or more of the aforementioned disadvantages and deficiencies. Another object of this invention is the provision of a foaming oxygenating mouthrinse in ready-to-use form having a pleasant flavor and/or color and enhanced stability in storage. Still another object of this invention is the provision of such a mouthrinse having a basis of the readily available, highly effective and economical hydrogen peroxide. Other objects and advantages will appear as the description proceeds.

The attainment of one or more of the above objects is made possible by this invention which comprises:
an aqueous oral solution containing, approximately by weight:
A. 1-3% of hydrogen peroxide,
B. 3-15% of a polyhydric alcohol selected from the group consisting of glycerin and sorbitol,
C. 3-10% of ethanol
D. 0.5 to 3% of a nonionic water soluble polyoxyethylenated polyoxypropylene polyol surfactant,
E. 0.3-2% of a nonionic surface active water soluble polyoxyethylenated monoester of sorbitol with $C_{10-18}$ fatty acid,
F. an effective sweetening amount of a sweetener compound, and
G. an effective flavoring amount of a flavor selected from the group consisting of
g1. wintergreen flavor containing methyl salicylate and menthol in a weight ratio of about 3:1 to 5:1, and
g2. cinnamon flavor being a propylene glycol solution containing about 6-9% menthol, 32-38% cinnamic aldehyde and 6-9% clove oil.

The aforementioned component G flavors have surprisingly been found to be satisfactorily stable and compatible in the presence of hydrogen peroxide, in contrast to other flavors, e.g. fruity flavors such as orange, lemon and lime, and even minty flavors other than the aforesaid g1 component wintergreen flavor, such as peppermint and spearmint. The other aforementioned components are similarly stable and compatible, in contrast to other usually known excipients. The critical combination of the aforementioned components A-G has been found to enable the attainment of the above-mentioned objects of this invention. Effective flavor amounts are as desired, typically ranging from about 0.05 to 1.0%, preferably about 0.1 to 0.5%, by weight in the solution.

A coloring agent is also often desirable for enhanced appearance and acceptability, but must be carefully selected for compatibility with the other named components, particularly the hydrogen peroxide. Green coloring agents for example have been generally found to be unacceptable in this regard. FD & C Blue No. 1 and Red No. 40 have been found to satisfy the requirements of this invention, employed in effective coloring amounts as desired, typically in concentrations of about 0.0002 to 0.004% by weight in the solution.

The preferred component F sweetener compound is saccharin, expecially sodium saccharin, but other known orally acceptable sweetener compounds may be employed, typically in concentrations of about 0.01 to 5 wt. %, such as xylitol, sodium cyclamate, perillartine, D-trypotophan, aspartame, dihydrochalcones and the like.

The component D nonionic surfactant is well known, being a block polymer readily available under the Pluronic trademark. These surfactants are straight chain polymers containing a hydrophobic (water insoluble) polyoxypropylene moiety polyoxyethylenated at both ends with sufficient water-solubilizing oxyethylene groups to achieve the desired water-solubility, HLB (hydrophyliclipophylic balance) and dispersing surfactant activity. The solid F series of Pluronics are preferred in which the molecular weight of the polyoxypropylene moiety ranges from about 950 to 4,000 and constitutes about 20-30% of the molecule (i.e. 80-70% polyoxyethylene in the molecule). Pluronic F 108 is especially preferred, in which the said hydrophobic moiety has a molecular weight of about 3250 and constitutes about 20% of the molecule. This surfactant has a molecular weight of about 14,000-16,000 and an HLB of about 28.

The component E nonionic surfactant is also well known under the generic term "polysorbate," being readily available under the Tween and other trademarks. These surfactants are mixtures of $C_{10-18}$ fatty acid esters of sorbitol (and sorbitol anhydrides), consisting predominantly of the monoester, condensed with about 10-30, preferably about 20, moles of ethyleneoxide. The fatty acid (aliphatic hydrocarbyl monocarboxylic acid) may be saturated or unsaturated, e.g. lauric, palmitic, stearic, oleic acids. Polysorbate 20(e.g. Tween 20) is especially preferred, commonly referred to as polyoxyethylene (20) sorbitan monolaurate.

The surfactant components serve as solubilizing, dispersing, emulsifying, wetting and viscosity-control agents in combination, being especially effective to solubilize the flavor.

Sorbitol is preferred as the component B polyhydric alcohol since although glycerin is sufficiently compatible with the other components, particularly the hydrogen peroxide, it interferes with at least 1 common method for analysis of the peroxide content. Component B serves as humectant, carrier (with the ethanol) and viscosity-control agent.

The solutions of this invention may contain other functional agents such as anticaries agents and the like. Fluorine-providing anticaries compounds optionally present in these solutions may be partially or fully water-soluble. They are characterized by their ability to release fluorine-containing ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, calcium fluoride, a copper fluoride such as cuprous fluoride, zinc fluoride, a tin fluoride such as stannic fluoride or stannous chlorofluoride, barium fluoride, sodium fluorosilicate, ammonium fluorosilicate, sodium florozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of the fluorine-providing compound is dependent to some extent upon the type of compound, its solubility, and the type of oral preparation, but it must be a nontoxic amount. An amount of such compound which releases a maximum of about 1% of fluoride ion by weight of the preparation is considered satisfactory. Any suitable minimum amount of such compound may be used, but it is preferable to employ sufficient compound to release about 0.005 to 1%, and preferably about 0.1% of fluoride ion. Typically, especially in the cases of MFP, alkali metal fluorides and stannous fluoride, this component is optionally present in these solutions in an amount of about 0.01 to 2 wt. %, preferably about 0.05 to 1 wt. %, especially about 0.76 wt. %.

The pH of the solutions of this invention generally range from about 4 to 6, preferably about 5. Other common mouthrinse excipients may be included in these solutions such as thickeners, preservatives, and the like. The solutions of this invention may be prepared by judiciously mixing the various components for proper solubilization in the ethanol/polyhydric alcohol/water carrier medium, coloring agent and hydrogen peroxide in order being preferably added after the other components.

The following examples of preferred embodiments of this invention are only illustrative. All amounts and proportions referred to herein and in the appended claims are by weight unless otherwise indicated. Typically, in preparing these exemplified formulations, the flavor is first added to the ethanol with agitation. The component D and E surfactants are then slowly sprinkled in with constant stirring, after which sufficient water is added slowly with stirring for abou ten minutes or until all the surfactants are dissolved and the solution is clear. The component B polyhydric alcohol is then added slowly with stirring followed by addition of the component F sweetener, preferably previously solubilized in a little water. Coloring agent, hydrogen peroxide (in the form of a 35% aqueous solution), and the remainder of the water are then added in succession.

TABLE I

| | Examples (% w/v) | | | | | |
|---|---|---|---|---|---|---|
| | 1 | 2 | 3 | 4 | 5 | 6 |
| Ethanol[1] | 4.75 | 4.75 | 4.75 | 4.75 | 4.75 | 4.75 |
| Wintergreen Flavor[2] | 0.22 | 0.22 | 0.22 | | | 0.22 |
| Cinnamon Flavor[3] | | | | 0.15 | 0.15 | |
| Pluronic F 108 | 1.0 | 1.0 | 1.0 | 1.0 | 1.0 | 1.0 |
| Polysorbate 20[4] | 0.6 | 0.6 | 0.6 | 0.6 | 0.6 | 0.6 |
| Sorbitol[5] | 10.5 | | | 10.5 | 10.5 | |
| Glycerin | | 5.0 | | | 5.0 | 5.0 |
| Sodium saccharin | 0.04 | 0.04 | 0.04 | 0.04 | 0.04 | 0.04 |
| FD & C Blue No. 1[6] | .0004 | .0004 | | | | |
| FD & C Red No. 40[6] | | | | | .002 | .002 |
| Hydrogen peroxide[7] | 1.5 | 1.5 | 1.5 | 1.5 | 1.5 | 1.5 |
| Purified Water (USP Deionized) | ← | qs. | to | 100 v. | → | → |

[1] in form of 95% soln
[2] 80% methyl salicylate, 20% menthol
[3] 7.5% menthol, 35% cinnamic aldehyde, 7.5% clove oil in propylene glycol soln.
[4] Tween 20-polyoxyethylene (20) sorbitan monolaurate
[5] in form of 70% soln
[6] in form of 1% soln
[7] in form of 35% soln All the above-exemplified formulations represent satisfactory, pleasing, acceptable and effective foaming oxygenating mouthrinses having satisfactory storage stability with respect to flavor, color, appearance, taste, peroxy content and the like.

This invention has been disclosed with respect to preferred embodiments, and various modifications and variations thereof obvious to those skilled in the art are to be included within the spirit and purview of this application and the scope of the appended claims.

We claim:

1. An aqueous oral solution containing, approximately by weight:
   A. 1–3% of hydrogen peroxide,
   B. 3–15% of a polyhydric alcohol selected from the group consisting of glycerin and sorbitol,
   C. 3–10% of ethanol
   D. 0.5 to 3% of a nonionic water soluble polyoxyethylenated polyoxypropylene polyol surfactant,
   E. 0.3–2% of a nonionic surface active water soluble polyoxyethylenated monoester of sorbitol with $C_{10-18}$ fatty acid,
   F. an effective sweetening amount of a sweetener compound, and
   G. an effective flavoring amount of a flavor selected from the group consisting of,
   g1. wintergreen flavor containing methyl salicylate and menthol in a weight ratio of about 3:1 to 5:1, and
   g2. cinnamon flavor being a propylene glycol solution containing about 6–9% menthol, 32–38% cinnamic aldehyde and 6–9% clove oil.

2. A solution according to claim 1 wherein the polyoxypropylene moiety in D has a molecular weight of about 3250 and constitutes about 20% of the total surfactant molecule.

3. A solution according to claim 2 wherein component E is polyoxyethylene (20) sorbitan monolaurate.

4. A solution according to claim 3 containing wintergreen flavor g1.

5. A solution according to claim 4 wherein component B is sorbitol.

6. A solution according to claim 5 wherein component F is sodium saccharin and the solution contains an effective coloring amount of FD & C Blue No. 1.

7. A solution according to claim 4 wherein component B is glycerin.

8. A solution according to claim 7 containing an effective coloring amount of FD & C Blue No. 1 and component F is sodium saccharin.

9. A solution according to claim 3 containing cinnamon flavor g2.

10. A solution according to claim 9 wherein component B is sorbitol.

11. A solution according to claim 10 containing an effective coloring amount of FD & C Red No. 40 and component F is sodium saccharin.

12. A solution according to claim 9 wherein component B is glycerin.

13. A solution according to claim 12 containing an effective coloring amount of FD & C Red No. 40 and component F is sodium saccharin.

14. An aqueous oral solution containing approximately by weight:
A. 1.5% of hydrogen peroxide,
B. 10.5% of sorbitol,
C. 4.75% of ethanol,
D. 1% of a nonionic water soluble polyoxyethylenated polyoxypropylene polyol surfactant wherein the polyoxypropylene moiety has a molecular weight of about 3250 and constitutes about 20% of the molecule,
E. 0.6% of polyoxyethylene (20) sorbitan monolaurate,
F. an effective sweetening amount of sodium saccharin, and
G. an effective flavoring amount of wintergreen flavor containing methyl salicylate and menthol in weight ratio of about 4:1.

15. A solution according to claim 14 further containing an effective coloring amount of FD & C Blue No. 1.

16. An aqueous oral solution containing, approximately by weight:
A. 1.5% of hydrogen peroxide,
B. 10.5% of sorbitol,
C. 4.75% of ethanol,
D. 1% of a nonionic water soluble polyoxyethylenated polyoxypropylene polyol surfactant wherein the polyoxypropylene moiety has a molicular weight of about 3250 and constitutes about 20% of the molecule,
E. 0.6% of polyoxyethylene (20) sorbitan monolaurate,
F. an effective sweetening amount of sodium saccharin, and
G. an effective flavoring amount of cinnamon flavor being a propylene glycol solution containing about 7.5% menthol, 35% cinnamic aldehyde and 7.5% of clove oil.

17. A solution according to claim 16 further containing an effective coloring amount of FD & C Red No. 40.

* * * * *